(12) United States Patent
De Lombaert et al.

(10) Patent No.: US 11,708,365 B2
(45) Date of Patent: Jul. 25, 2023

(54) PROCESSES FOR PREPARING TPH1 INHIBITORS

(71) Applicant: ALTAVANT SCIENCES GmbH, Basel (CH)

(72) Inventors: Stéphane De Lombaert, Brisbane, CA (US); Daniel R. Goldberg, Seattle, WA (US)

(73) Assignee: Altavant Sciences GmbH

( * ) Notice: Subject to any disclaimer, the term of this patent is extended or adjusted under 35 U.S.C. 154(b) by 54 days.

(21) Appl. No.: 17/149,070

(22) Filed: Jan. 14, 2021

(65) Prior Publication Data

US 2021/0139481 A1     May 13, 2021

Related U.S. Application Data

(63) Continuation of application No. 16/407,375, filed on May 9, 2019, now abandoned, which is a continuation of application No. PCT/IB2017/001594, filed on Nov. 9, 2017.

(60) Provisional application No. 62/419,557, filed on Nov. 9, 2016.

(51) Int. Cl.
    *C07D 471/10*         (2006.01)
(52) U.S. Cl.
    CPC ................................... *C07D 471/10* (2013.01)
(58) Field of Classification Search
    CPC .................................................... C07D 471/10
    See application file for complete search history.

(56) References Cited

U.S. PATENT DOCUMENTS

| | | | |
|---|---|---|---|
| 3,682,925 | A | 8/1972 | Hollander et al. |
| 3,904,632 | A | 9/1975 | Hollander et al. |
| 4,859,771 | A | 8/1989 | Reider et al. |
| 5,030,725 | A | 7/1991 | Rieck, III et al. |
| 8,476,290 | B2 | 7/2013 | Yoshida |
| 8,809,589 | B2 | 8/2014 | Gore et al. |
| 9,199,994 | B2 | 12/2015 | De Lombaert et al. |
| 9,750,740 | B2 | 9/2017 | De Lombaert et al. |
| 2013/0331575 | A1 | 12/2013 | Dancer |

FOREIGN PATENT DOCUMENTS

| | | |
|---|---|---|
| CN | 1053920 A | 8/1991 |
| CN | 103429577 A | 12/2013 |
| CN | 103896779 A | 7/2014 |
| CN | 105764902 A | 7/2016 |
| EP | 2444402 A1 | 4/2012 |
| JP | S50-39652 B1 | 12/1975 |
| WO | 2010147094 A1 | 12/2010 |

OTHER PUBLICATIONS

Chinese Search Report for corresponding Chinese application CN 201780069288X, 6 pages, dated Jun. 26, 2021.
Chinese First Office Action for corresponding Chinese application CN 201780069288X, 23 pages, dated Jul. 1, 2021.
Japanese First Office Action for corresponding application JP2019-525887, 14 pages, dated Apr. 6, 2021.
Arai, "Isomerization-Crystallization Method in Optical Resolution", Journal of Synthetic Organic Chemistry, 1986 vol. 14, pp. 486-498, Japan.
Yamada et al. "Method for the Racemization of Optically Active Amino Acids", Journal of Organic Chemistry, 1983, 48 (60), pp. 843-846.
Bathori et al "One hydrogen bond does not a separation make, or does it? Resolution of amines by diacetonegetogulonic acid", ChemComm, vol. 51, No. 26. Feb. 17, 2015, pp. 5664-5667, Royal Society of Chemistry.
International Search Report for International Application No. PCT/IB2017/001594, 4 pages, dated Mar. 20, 2018.
Written Opinion of the International Searching Authority for International Application No. PCT/IB2017/001594, 5 pages, dated Mar. 20, 2018.
European Office Action for corresponding application EP17838138.0, 4 pages, dated Apr. 21, 2020.
International Preliminary Report on Patentability for International Application No. PCT/IB2017/001594, 3 pages, dated May 14, 2019.
European Office Action for corresponding application EP17838138.0, 3 pages, dated Nov. 12, 2020.

*Primary Examiner* — David K O'Dell
(74) *Attorney, Agent, or Firm* — Fox Rothschild LLP

(57) ABSTRACT

The present disclosure is directed to intermediates and salts thereof useful for the preparation of spirocyclic compounds which are inhibitors of tryptophan hydroxylase (TPH), particularly isoform 1 (TPH1). Processes of preparing the intermediates, salts, and TPH inhibitors are also provided.

25 Claims, No Drawings

PROCESSES FOR PREPARING TPH1 INHIBITORS

CROSS-REFERENCE TO RELATED APPLICATIONS

The present application is a continuation application of U.S. Ser. No. 16/407,375, filed May 9, 2019, which is a continuation application of PCT/IB2017/001594, filed Nov. 9, 2017, which claims priority from U.S. Provisional Application No. 62/419,557, filed Nov. 9, 2016, both of which are incorporated herein by reference in their entireties.

BACKGROUND OF THE DISCLOSURE

1. Field of the Invention

The present disclosure is directed to a process of preparing intermediates useful for the preparation of spirocyclic compounds which are inhibitors of tryptophan hydroxylase (TPH), particularly isoform 1 (TPH1), that are useful in the treatment of diseases or disorders associated with peripheral serotonin including, for example, gastrointestinal, cardiovascular, pulmonary, inflammatory, metabolic, and low bone mass diseases, as well as serotonin syndrome, and cancer.

2. Description of the Prior Art

Serotonin (5-hydroxytryptamine, 5-HT) is a neurotransmitter that modulates central and peripheral functions by acting on neurons, smooth muscle, and other cell types. 5-HT is involved in the control and modulation of multiple physiological and psychological processes. In the central nervous system (CNS), 5-HT regulates mood, appetite, and other behavioral functions. In the GI system, 5-HT plays a general prokinetic role and is an important mediator of sensation (e.g., nausea and satiety) between the GI tract and the brain. Dysregulation of the peripheral 5-HT signaling system has been reported to be involved in the etiology of several conditions such as osteoporosis, cancer, cardiovascular diseases, diabetes, atherosclerosis, as well as gastrointestinal, pulmonary, inflammatory, and liver diseases or disorders.

Two vertebrate isoforms of TPH, namely TPH1 and TPH2, have been identified. TPH1 is primarily expressed in the pineal gland and non-neuronal tissues, such as enterochromaffin (EC) cells located in the gastrointestinal (GI) tract. TPH2 (the dominant form in the brain) is expressed exclusively in neuronal cells, such as dorsal raphe or myenteric plexus cells. The peripheral and central systems involved in 5-HT biosynthesis are isolated, with 5-HT being unable to cross the blood-brain barrier. Therefore, the pharmacological effects of 5-HT can be modulated by agents affecting TPH in the periphery, mainly TPH1 in the gut.

Recent reports have described the development of new spirocyclic TPH1 inhibitors useful for selectively reducing intestinal 5-HT levels as a means for treating and preventing 5-HT-associated diseases (see e.g., U.S. Pat. No. 9,199,994, the disclosure of which is incorporated herein by reference in its entirety). The processes of the present disclosure are useful for preparing TPH1 inhibitors described in U.S. Pat. No. 9,199,994, such as (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate.

SUMMARY OF THE DISCLOSURE

The present disclosure provides, inter alia, a process of increasing the amount of an isomeric compound of Formula I-(S):

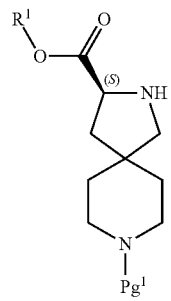

relative to an amount of an isomeric compound of Formula I-(R):

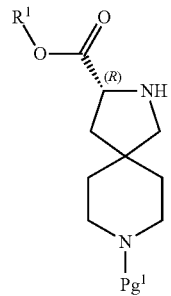

in a starting mixture comprising both isomeric compounds of Formula I-(S) and Formula I-(R), the process comprising:

reacting the starting mixture with 2,3:4,6-di-O-isopropylidene-2-keto-L-gulonic acid, or a hydrate thereof, in the presence of an aldehyde to form a salt mixture comprising 2,3:4,6-di-O-isopropylidene-2-keto-L-gulonic acid salts of the isomeric compounds, wherein the salt mixture has an increased amount of the gulonic acid salt of the isomeric compound of Formula I-(S) relative to the amount of gulonic acid salt of the isomeric compound of Formula I-(R) when compared with the relative amounts of the isomeric compounds of Formulas I-(S) and I-(R) present in the starting mixture, and wherein constituent variables are defined herein.

The present disclosure further provides a mixture of isomeric compounds having Formulas I-(S) and I-(R), wherein the enantiomeric excess of the isomeric compound of Formula I-(S) is about 90% or greater.

The present disclosure further provides a 2,3:4,6-di-O-isopropylidene-2-keto-L-gulonic acid salt of the isomeric compounds of Formula I-(S) or Formula I-(R).

The details of one or more embodiments of the disclosure are set forth in the accompanying drawings and the description below. Other features, objects, and advantages of the disclosure will be apparent from the description and drawings, and from the claims.

DETAILED DESCRIPTION OF THE DISCLOSURE

The present application provides, inter alia, a process of increasing the amount of an isomeric compound of Formula I-(S):

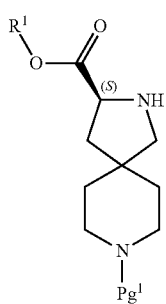

wherein R¹ is $C_{1-6}$ alkyl and $Pg^1$ is an amino protecting group, relative to an amount of an isomeric compound of Formula I-(R):

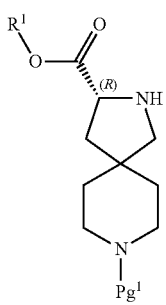

in a starting mixture comprising both isomeric compounds of Formula I-(S) and Formula I-(R), the process comprising:

reacting the starting mixture with 2,3:4,6-di-O-isopropylidene-2-keto-L-gulonic acid, or a hydrate thereof, in the presence of an aldehyde to form a salt mixture comprising 2,3:4,6-di-O-isopropylidene-2-keto-L-gulonic acid salts of the isomeric compounds, wherein the salt mixture has an increased amount of the gulonic acid salt of the isomeric compound of Formula I-(S) relative to the amount of gulonic acid salt of the isomeric compound of Formula I-(R) when compared with the relative amounts of the isomeric compounds of Formulas I-(S) and I-(R) present in the starting mixture.

In some embodiments, the 2,3:4,6-di-O-isopropylidene-2-keto-L-gulonic acid, or a hydrate thereof, used in the reaction is 2,3:4,6-di-O-isopropylidene-2-keto-L-gulonic acid monohydrate. In some embodiments, the reacting is carried out with about 1 molar equivalent of the 2,3:4,6-di-O-isopropylidene-2-keto-L-gulonic acid, or a hydrate thereof, with respect to the combined amount of both isomeric compounds of Formula I-(S) and Formula I-(R) in the starting mixture.

In some embodiments, the aldehyde used in the reaction is an aromatic aldehyde such as benzaldehyde. The amount of aldehyde can be used in a catalytic amount with respect to the combined amount of both isomeric compounds of Formula I-(S) and Formula I-(R) in the starting mixture. In some embodiments, the reacting is carried out with less than 1 molar equivalent of the aldehyde with respect to the combined amount of both isomeric compounds of Formula I-(S) and Formula I-(R) in the starting mixture, for example, less than 1 molar equivalent, less than 0.8 molar equivalents, less than 0.6 molar equivalents, less than 0.4 molar equivalents, less than 0.2 molar equivalents, or less than 0.1 molar equivalents. In some embodiments, the reacting is carried out with about 0.01 to about 0.5 molar equivalents of the aldehyde with respect to the combined amount of both isomeric compounds of Formula I-(S) and Formula I-(R) in the starting mixture, for example, about 0.01 to about 0.5, about 0.01 to about 0.4, about 0.01 to about 0.3, about 0.01 to about 0.2, or about 0.01 to about 0.1 molar equivalents. In further embodiments, the reaction can be carried out, at least at some point during the reaction, at an elevated temperature. In some embodiments, the temperature can range from about 35° C. to about 45° C., about 30° C. to about 40° C., about 25° C. to about 35° C., about 20° C. to about 30° C., or about 15° C. to about 25° C. A solvent may also be used to carry out the reaction, such as an organic solvent (e.g., an ether solvent such as 2-methyltetrahydrofuran).

In some embodiments, the enantiomeric excess of the gulonic acid salt of the isomeric compound of Formula I-(S) is about 75% or greater, about 80% or greater, about 85% or greater, about 90% or greater, about 95% or greater, about 97% or greater, about 98% or greater, or about 99% or greater.

In some embodiments, the enantiomeric excess of the gulonic acid salt of the isomeric compound of Formula I-(S) can range from about 75% to about 99.9%, about 80% to about 99.9%, about 85% to about 99.9%, about 90% to about 99.9%, about 95% to about 99.9%, about 96% to about 99.9%, about 97% to about 99.9%, about 98% to about 99.9%, about 99% to about 99.9%, or about 99.5% to about 99.9%.

In some embodiments, the process further comprises purifying the salt mixture (e.g., via recrystallization) to form a purified salt mixture having an increased amount of the gulonic acid salt of the isomeric compound of Formula I-(S) relative to the gulonic acid salt of the isomeric compound of Formula I-(R) when compared with the relative amounts of the gulonic acid salts of the isomeric compounds prior to the purification. The purification can be carried out in a solvent such as an organic solvent (e.g., an ether solvent such as 2-methyltetrahydrofuran).

In some embodiments, the enantiomeric excess of the gulonic acid salt of the isomeric compound of Formula I-(S) after the purifying step is about 90% or greater, about 95% or greater, about 96% or greater, about 97% or greater, about 98% or greater, or about 99% or greater.

In some embodiments, the enantiomeric excess of the gulonic acid salt of the isomeric compound of Formula I-(S) after the purifying step can range from about 90% to about 99.9%, about 95% to about 99.9%, about 96% to about 99.9%, about 97% to about 99.9%, about 98% to about 99.9%, about 99% to about 99.9%, or about 99.5% to about 99.9%.

In some embodiments, the process further comprises reacting the purified salt mixture with a base to form a freebased mixture comprising isomeric compounds having Formula I-(S) and Formula I-(R):

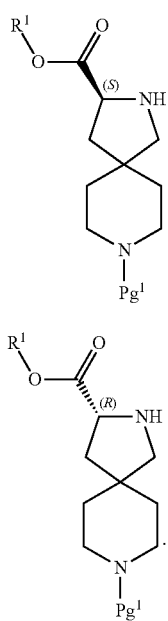

In some embodiments, the base used in the freebasing reaction is an alkali metal base such as sodium carbonate. The amount of base used can be in a molar excess with respect to the combined amount of gulonic acid salts in the salt mixture (e.g., greater than 1 molar equivalent with respect to the amount of gulonic acid salts in the salt mixture), or in any amount to that is sufficient to convert the gluonic acid salts to freebase compounds. In some embodiments, the amount of base used in the freebasing reaction is from about 1.1 to about 100 molar equivalents, about 1.1 to about 50 molar equivalents, about 1.1 to about 25 molar equivalents, about 1.1 to about 10 molar equivalents, or about 1.1 to about 5 molar equivalents with respect to the amount of gulonic acid salts in the salt mixture. In further embodiments, the base is provided as an aqueous solution, such as a 10% aqueous solution, a 20% aqueous solution, a 30% aqueous solution, a 40% aqueous solution, and the like. The freebasing reaction can further be carried out, at least at some point during the reaction, at an elevated temperature. In some embodiments, the temperature can range from about 10° C. to about 30° C., about 15° C. to about 25° C., or about 15° C. to about 20° C. A solvent may also be used to carry out the freebasing reaction, such as an organic solvent comprising an ether solvent (e.g., a furan such as 2-methyltetrahydrofuran) or hydrocarbon solvent (e.g., such as n-heptane), or a combination thereof.

In some embodiments, the enantiomeric excess of the isomeric compound of Formula I-(S) in the freebased mixture is about 90% or greater, about 95% or greater, about 97% or greater, about 98% or greater, about 99% or greater, or about 99.9% or greater.

In some embodiments, the enantiomeric excess of the isomeric compound of Formula I-(S) in the freebased mixture can range from about 90% to about 99.9%, about 95% to about 99.9%, about 96% to about 99.9%, about 97% to about 99.9%, about 98% to about 99.9%, about 99% to about 99.9%, or about 99.5% to about 99.9%.

As used herein, the term "$C_{i-j}$ alkyl," employed alone or in combination with other terms, refers to a saturated hydrocarbon group that may be straight-chain or branched, having i to j carbon atoms. In some embodiments, the alkyl group contains from 1 to 6, 1 to 4, or from 1 to 3 carbon atoms. Examples of alkyl moieties include, but are not limited to, chemical groups such as methyl, ethyl, n-propyl, isopropyl, n-butyl, s-butyl, t-butyl, n-pentyl, and n-hexyl. In some embodiments, $R^1$ is ethyl.

Processes for preparing of the compounds and salts described herein can involve the protection and deprotection of various chemical groups (e.g, protection and deprotection of amine groups with an amino protecting group). The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety. Adjustments to the protecting groups and formation and cleavage methods described herein may be adjusted as necessary in light of the various substituents.

For example, appropriate $Pg^1$ protecting groups include, but are not limited to the protecting groups for amines described in Wuts and Greene, Protective Groups in Organic Synthesis, 4th ed., John Wiley & Sons: New Jersey, pages 696-887 (and, in particular, pages 872-887) (2007), the disclosure of which is incorporated herein by reference in its entirety. Example amino protecting groups include, but are not limited to, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), tert-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP), tri($C_{1-4}$ alkyl)silyl (e.g., tri(isopropyl)silyl), 1,1-diethoxymethyl, or N-pivaloyloxymethyl (POM). In some embodiments, $Pg^1$ is tert-butoxycarbonyl.

In some embodiments, the starting mixture comprising both isomeric compounds of Formula I-(S) and Formula I-(R) is prepared according to a process comprising reacting a compound of Formula II:

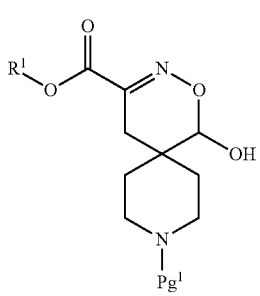

with hydrogen gas in the presence of a hydrogenation catalyst, wherein $R^1$ is $C_{1-6}$ alkyl and $Pg^1$ is an amino protecting group. In some embodiments, $R^1$ is ethyl. In some embodiments, $Pg^1$ is tert-butoxycarbonyl.

As used herein, the term "hydrogenation catalyst" refers to a metal (e.g., palladium, nickel, or rhodium) catalyst suitable to catalyze a hydrogenation reaction (i.e., reaction of a compound with hydrogen gas). Example hydrogenation catalysts include, but are not limited to, palladium on carbon, Lindlar's catalyst (palladium deposited on calcium carbonate or barium sulfate), Raney Ni (e.g., Raney Ni A5000), Wilkinson's catalyst, HRuCl(PPh$_3$)$_3$, RhCl(PPh$_3$)$_3$, [Rh(COD)Cl]$_2$, [Ir(COD)(PMePh$_2$)$_2$]$^+$, [Rh(1,5-cyclooctadiene)(PPh$_3$)$_2$]$^+$, PtO$_2$ (Adam's catalyst), palladium on carbon, palladium black, and the like. Additional examples of hydrogenation catalysts may be found in Nishimura, Heterogeneous Catalytic Hydrogenation for Organic Synthesis, Edition 1, Wiley (Apr. 17, 2001) and Chaloner, Homogeneous Hydrogenation, Edition 1, Springer Netherlands (Dec. 6, 2010), the disclosure of each of which is incorporated by reference herein in its entirety.

In some embodiments, the hydrogenation catalyst used in the reaction is Raney Ni A5000. The hydrogenation catalyst can be used in a catalytic amount with respect to the amount of the compound of Formula II used in the reaction. A solvent may also be used to carry out the hydrogenation reaction, such as an organic solvent comprising a protic solvent (e.g., ethanol), or an ether solvent (e.g., a furan solvent such as tetrahydrofuran), or a combination thereof. In further embodiments, the reaction can be carried out, at least at some point during the reaction, at an elevated temperature. In some embodiments, the temperature can range from about 30° C. to about 45° C., about 30° C. to about 40° C., or about 35° C. to about 40° C.

In some embodiments, the compound of Formula II is prepared according to a process comprising reacting a compound of Formula III:

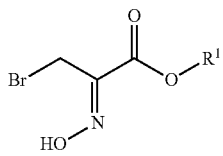

III with a compound of Formula IV:

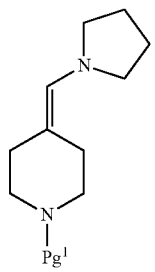

IV in the presence of a base, wherein R$^1$ is C$_{1-6}$ alkyl and Pg$^1$ is an amino protecting group. In some embodiments, R$^1$ is ethyl. In some embodiments, Pg$^1$ is tert-butoxycarbonyl.

In some embodiments, the base used in the reaction of the compounds of Formula III and IV is an amine base such as pyridine, triethylamine, or N,N-diisopropylethylamine. The amount of base used can be a molar excess with respect to the amount of the compound of Formula IV. In some embodiments, the amount of base used can range from about 1.1 to about 3 molar equivalents, about 1.1 to about 2 molar equivalents, about 1.4 to about 2 molar equivalents, or about 1.4 to about 1.8 molar equivalents with respect to 1 molar equivalent of the compound of Formula III. In some embodiments, the reacting is carried out using about 1 molar equivalent of the compound of Formula III with respect to 1 molar equivalent of the compound of Formula IV. In further embodiments, the reaction can be carried out, at least at some point during the reaction, at a temperature that is about room temperature or lower. In some embodiments, the temperature can range from about −10° C. to about 25° C., about −10° C. to about 20° C., about 0° C. to about 20° C., about 0° C. to about 15° C., or about 10° C. to about 15° C. A solvent may also be used to carry out the reaction, such as an organic solvent comprising a hydrocarbon solvent (e.g., toluene), or an ether solvent (e.g., a furan solvent such as 2-methyltetrahydrofuran), or a combination thereof.

In some embodiments, the compound of Formula III is prepared according to a process comprising reacting a compound of Formula V:

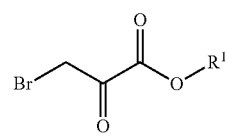

V with hydroxylamine, or a salt thereof, wherein R$^1$ is C$_{1-6}$ alkyl. In some embodiments, R$^1$ is ethyl.

In some embodiments, the hydroxylamine is a hydroxylamine salt, such as hydroxylamine hydrochloride. The amount of the hydroxylamine, or salt thereof, used can range from about 1.1 to about 2 molar equivalents, about 1.1 to about 1.8 molar equivalents, about 1.1 to about 1.6 molar equivalents, or about 1.1 to about 1.4 molar equivalents based on 1 molar equivalent of the compound of Formula V. In further embodiments, the reaction can be carried out, at least at some point during the reaction, at a temperature that is about room temperature or lower. In some embodiments, the temperature can range from about 10° C. to about 30° C., about 10° C. to about 25° C., or about 15° C. to about 25° C. A solvent may also be used to carry out the reaction, such as a hydrocarbon solvent (e.g., toluene), or a protic solvent (e.g., water), or a combination thereof.

In some embodiments, the compound of Formula IV is prepared according to a process comprising reacting a compound of Formula VI:

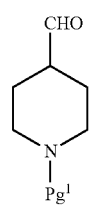

VI with pyrrolidine, wherein Pg$^1$ is an amino protecting group. In some embodiments, Pg$^1$ is tert-butoxycarbonyl.

The amount of pyrrolidine used can be a molar excess with respect to the amount of the compound of Formula VI used. In some embodiments, the amount of pyrrolidine used can range from about 1.1 to about 3 molar equivalents, about 1.1 to about 2 molar equivalents, or about 1.1 to about 1.8 molar equivalents with respect to 1 molar equivalent of the compound of Formula VI. A solvent may also be used to carry out the reaction, such as an organic solvent (e.g., a hydrocarbon solvent such as toluene). In further embodiments, the reaction can be carried out, at least at some point during the reaction, at an elevated temperature. In some embodiments, the reaction can be carried out at the solvents boiling temperature.

In some embodiments, the present application provides a process of increasing the amount of an isomeric compound of Formula Ia-(S):

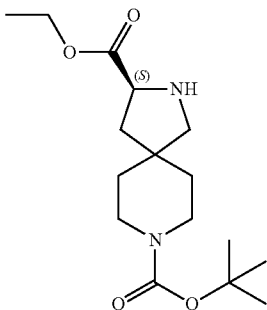

relative to an amount of an isomeric compound of Formula Ia-(R):

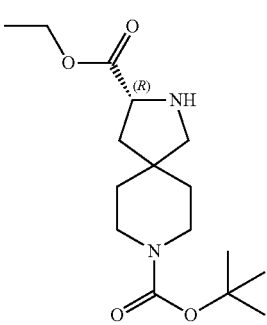

in a starting mixture comprising both isomeric compounds of Formula Ia-(S) and Formula Ia-(R), the process comprising:

reacting the starting mixture with 2,3:4,6-di-O-isopropylidene-2-keto-L-gulonic acid monohydrate in the presence of benzaldehyde to form a salt mixture comprising 2,3:4,6-di-O-isopropylidene-2-keto-L-gulonic acid salts of the isomeric compounds, wherein the salt mixture has an increased amount of the gulonic acid salt of the isomeric compound of Formula Ia-(S) relative to the amount of gulonic acid salt of the isomeric compound of Formula Ia-(R) when compared with the relative amounts of the isomeric compounds of Formulas Ia-(S) and Ia-(R) present in the starting mixture;

recrystallizing the salt mixture to form a purified salt mixture having an increased amount of the gulonic acid salt of the isomeric compound of Formula Ia-(S) relative to the gulonic acid salt of the isomeric compound of Formula Ia-(R) when compared with the relative amounts of the gulonic acid salts of the isomeric compounds prior to the purification; and reacting the purified salt mixture in the presence of sodium carbonate to form a freebased mixture comprising isomeric compounds having Formula Ia-(S) and Formula Ia-(R), wherein the enantiomeric excess of the isomeric compound of Formula Ia-(S) in the freebased mixture is greater than about 90%.

The starting mixture comprising both isomeric compounds of Formula I-(S) and Formula I-(R) may be prepared according to the embodiments described above and also, for example, as further illustrated by Scheme 1.

Scheme 1.

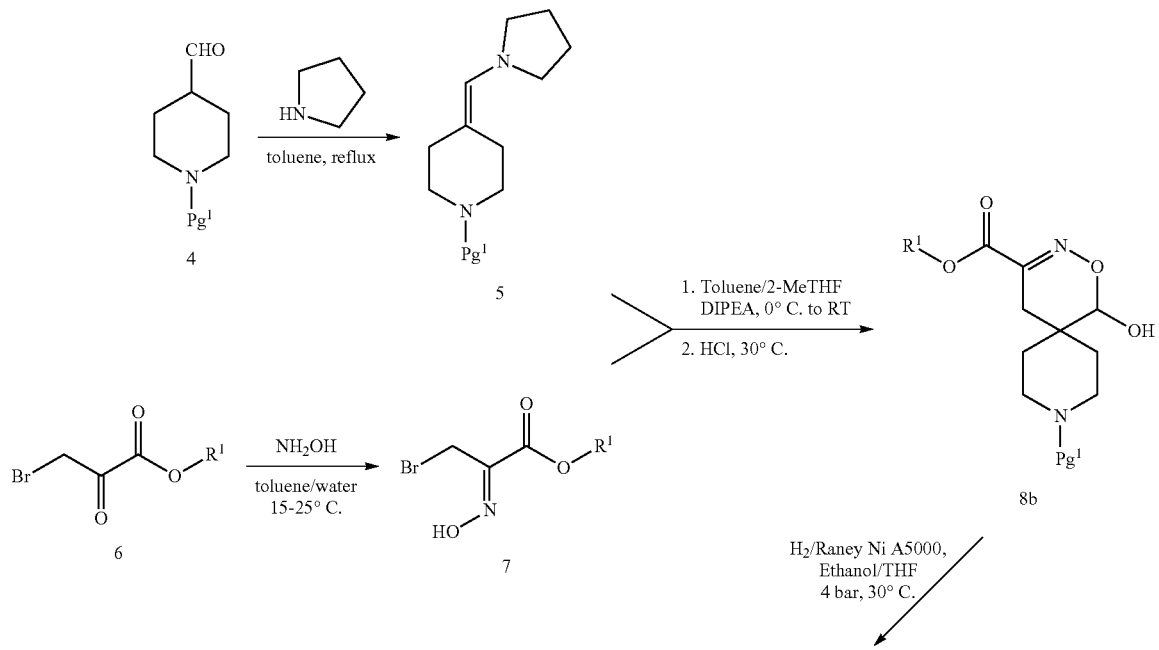

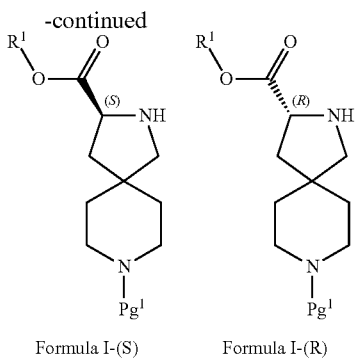

Formula I-(S)     Formula I-(R)

The salt mixture described herein having an increased amount of the gulonic acid salt of the isomeric compound of Formula I-(S) relative to the gulonic acid salt of the isomeric compound of Formula I-(R) (i.e., a salt mixture enriched in the isomeric compound of Formula I-(S)) may be prepared according to the embodiments described above and also, for example, as shown below in Scheme 2.

Scheme 2.

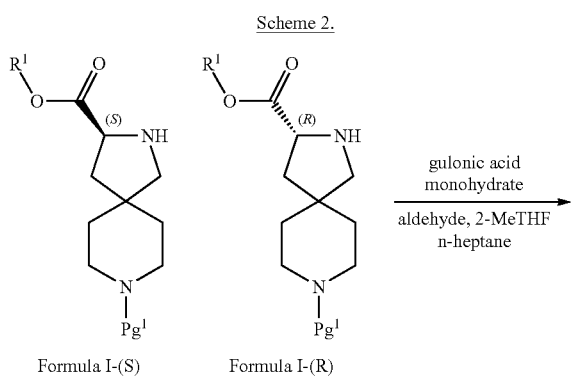

Formula I-(S)     Formula I-(R)

Formula I-(S) gulonic acid salt
(major isomeric product)

Formula I-(R) gulonic acid salt
(minor isomeric product)

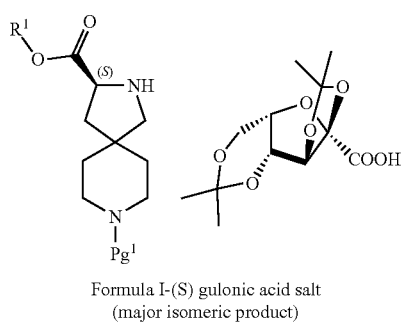

gulonic acid monohydrate = wherein $R^1$ is $C_{1-6}$ alkyl and $Pg^1$ is an amino protecting group.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more molar equivalents of second reagent are used with respect to the first reagent. The reacting steps of the processes described herein can be conducted for a time and under conditions suitable for preparing the identified product.

In some embodiments, preparation of compounds or salts can involve the addition of acids or bases to affect, for example, catalysis of a desired reaction or formation of salt forms such as acid addition salts (e.g. formation of a 2,3:4,6-di-O-isopropylidene-2-keto-L-gulonic acid salt).

Example acids can be inorganic or organic acids and include, but are not limited to, strong and weak acids. Some example acids include, but are not limited to, hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, nitric acid, 2,3:4,6-di-O-isopropylidene-2-keto-L-gulonic acid, acetic acid, propionic acid, butanoic acid, benzoic acid, tartaric acid, pentanoic acid, hexanoic acid, heptanoic acid, octanoic acid, nonanoic acid, and decanoic acid.

Some example bases include, but are not limited to, carbonates (e.g., sodium carbonate), bicarbonates (e.g., sodium bicarbonate), hydroxides (e.g., sodium hydroxide, potassium hydroxide), alkoxides, metal amides, metal hydrides, metal dialkylamides, and arylamines, wherein; alkoxides include lithium, sodium and potassium salts of methyl, ethyl and tert-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, i-propyl, n-butyl, t-butyl, trimethylsilyl and cyclohexyl substituted amides.

All compounds, and salts thereof, can be found together with other substances such as water and solvents (e.g., hydrates and solvates) or can be isolated.

As used herein, the term "enriched," refers to an increased amount of a particular compound or salt (e.g., an (S)-isomeric compound or salt) in a mixture when compared with the amount of the compound in the mixture prior to being enriched. In some embodiments, a mixture may be enriched in the amount of a first isomeric compound or salt (e.g., an (S)-isomeric compound or salt) relative to a second isomeric compound or salt (e.g., an (R)-isomeric compound) when compared with the relative amount of the isomeric compounds in a starting mixture (e.g., prior to forming the enriched mixture). For example, a mixture enriched in an isomeric compound or salt of Formula I-(S) has an increased amount of the isomeric compound of Formula I-(S) relative isomeric compound of Formula I-(R) when compared with the relative amounts of the isomeric compounds of Formulas I-(S) and I-(R) in a starting mixture (e.g. a racemic mixture of the isomeric compounds of Formulas I-(S) and I-(R)).

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable halogenated solvents include, but are not limited to, carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, I,I,I-trifluorotoluene, 1,2-dichloroethane, 1,2-dibromoethane, hexafluorobenzene, 1,2,4-trichlorobenzene, 1,2-dichlorobenzene, chlorobenzene, and fluorobenzene.

Suitable ether solvents include, but are not limited to, dimethoxymethane, tetrahydrofuran, 2-methyltetrahydrofuran, 1,3-dioxane, 1,4-dioxane, furan, diethyl ether, ethylene glycol dimethyl ether, ethylene glycol diethyl ether, diethylene glycol dimethyl ether (diglyme), diethylene glycol diethyl ether, triethylene glycol dimethyl ether, anisole, and t-butyl methyl ether.

Suitable protic solvents include but are not limited to, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable aprotic solvents include but are not limited to, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, and hexamethylphosphoramide.

Suitable hydrocarbon solvents include, but are not limited to, benzene, cyclohexane, pentane, hexane, toluene, cycloheptane, methylcyclohexane, n-heptane, ethylbenzene, m-, o-, or p-xylene, octane, indane, nonane, and naphthalene.

The reactions of the processes described herein can be carried out in air or under an inert atmosphere (e.g., nitrogen or argon atmosphere). Typically, reactions containing reagents or products that are substantially reactive with air can be carried out using air-sensitive synthetic techniques that are well known to the skilled artisan.

Upon carrying out preparation of compounds and salts according to the processes described herein, the usual isolation and purification operations such as concentration, filtration, extraction, solid-phase extraction, recrystallization, chromatography, and the like may be used, to isolate the desired products.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). For example, the expression, "room temperature," as used herein, is understood in the art and refer generally to a temperature (e.g. a reaction temperature) that is about the temperature of the room in which the reaction is carried out, for example, a temperature from about 20° C. to about 30° C.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds and Salts of the Invention

The present application further provides a mixture of isomeric compounds having Formulas I-(S) and I-(R):

I-(S)

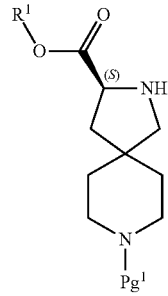

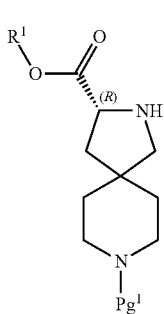

wherein $R^1$ is $C_{1-6}$ alkyl and $Pg^1$ is an amino protecting group, and wherein the enantiomeric excess of the isomeric compound of Formula I-(S) is about 90% or greater, about 95% or greater, about 97% or greater, about 98% or greater, about 99% or greater, or about 99.9% or greater. In some embodiments, $R^1$ is ethyl. In some embodiments, $Pg^1$ is tert-butoxycarbonyl.

In some embodiments, the enantiomeric excess of the isomeric compound of Formula I-(S) can range from about 90% to about 99.9%, about 95% to about 99.9%, about 96% to about 99.9%, about 97% to about 99.9%, about 98% to about 99.9%, about 99% to about 99.9%, or about 99.5% to about 99.9%.

In some embodiments, the mixture of isomeric compounds having Formulas I-(S) and I-(R) is prepared according to a process provided herein, wherein the mixture is enriched in the isomeric compound of Formula I-(S).

The present application further provides a 2,3:4,6-di-O-isopropylidene-2-keto-L-gulonic acid salt of the isomeric compound of Formula I-(S) or Formula I-(R):

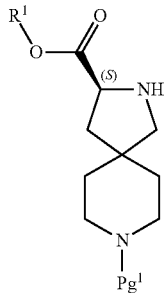

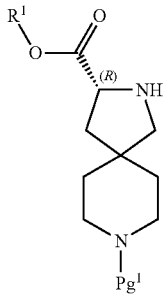

wherein $R^1$ is $C_{1-6}$ alkyl and $Pg^1$ is an amino protecting group. In some embodiments, $R^1$ is ethyl. In some embodiments, $Pg^1$ is tert-butoxycarbonyl.

In some embodiments, the salt is the 2,3:4,6-di-O-isopropylidene-2-keto-L-gulonic acid salt of the isomeric compound of Formula I-(S).

In some embodiments, the salt is the 2,3:4,6-di-O-isopropylidene-2-keto-L-gulonic acid salt of the isomeric compound of Formula I-(R).

In some embodiments, the 2,3:4,6-di-O-isopropylidene-2-keto-L-gulonic acid salt of the isomeric compound of Formula I-(S) or Formula I-(R) is prepared according to a process provided herein.

Compounds and salts of the disclosure can also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1, 2, 4-triazole, 1H- and 2H-isoindole, and 1H- and 2H-pyrazole.

The term "compound," as used herein, is meant to include all stereoisomers, geometric isomers, tautomers, and isotopes of the structures depicted. Compounds and salts herein identified by name or structure as one particular tautomeric form are intended to include other tautomeric forms unless otherwise specified. Compounds and salts herein identified by name or structure without specifying the particular configuration of a stereocenter are meant to encompass all the possible configurations at the stereocenter. For example, if a particular stereocenter in a compound of the disclosure could be R or S, but the name or structure of the compound does not designate which it is, than the stereocenter can be either R or S.

The compounds and salts described herein can be asymmetric (e.g., having one or more stereocenters). All stereoisomers, such as enantiomers and diastereoisomers, are intended unless otherwise indicated. Compounds and salts of the present disclosure that contain asymmetrically substituted carbon atoms can be isolated in optically active or racemic forms. Many geometric isomers of olefins, C=N double bonds, and the like can also be present in the compounds or salts described herein, and all such stable isomers are contemplated in the present disclosure. Cis and trans geometric isomers of the compounds of the present disclosure may be isolated as a mixture of isomers or as separated isomeric forms.

In some embodiments, the compounds or salts of the disclosure are substantially isolated. By "substantially isolated" is meant that the compound is at least partially or substantially separated from the environment in which it was formed or detected. Partial separation can include, for example, a composition enriched in the compounds of the disclosure. Substantial separation can include compositions containing at least about 50%, at least about 60%, at least about 70%, at least about 80%, at least about 90%, at least about 95%, at least about 97%, or at least about 99% by weight of the compounds or salts of the disclosure, or salt thereof. Methods for isolating compounds and their salts are routine in the art.

Compounds and salts of the disclosure can also include all isotopes of atoms occurring in the intermediates or final compounds. Isotopes include those atoms having the same atomic number but different mass numbers. For example, isotopes of hydrogen include tritium and deuterium.

Synthesis of TPH1 Inhibitors

The salt mixture enriched in the isomeric compound of Formula I-(S) described herein may be further reacted, for example, to prepare intermediates useful for the preparation of compounds which are TPH1 inhibitors, as shown below in Scheme 3. For example, the salt mixture enriched in the isomeric compound of Formula I-(S) is prepared according to one or more embodiments described herein (Step 1), and the free-base form of the isomeric compound of Formula I-(S) is subsequently formed (e.g., via reaction with sodium carbonate) and isolated (Step 2). The free amine of the isomeric compound of Formula I-(S) can then protected using standard amine protection conditions as shown in Step 3, for example, reaction with Pg²-X in the presence of a base (e.g., trimethylamine), wherein Pg² is an amino protecting group (e.g., tert-butoxycarbonyl, carbobenzyloxy, and the like) and X is halo (e.g., Cl). Selective deprotection of the amino protecting group Pg¹ (Step 4) forms the desired Intermediate 1, an intermediate useful in the preparation of compounds which are TPH1 inhibitors.

Intermediate 1 may be used in the preparation of TPH1-inhibiting compounds, for example, as shown below in Scheme 4, wherein $R^1$ is $C_{1-6}$ alkyl, $Pg^2$ is an amino protecting group, and variables W, X, Y, $R^2$, $R^3$, $R^A$, $R^B$, $R^C$, $R^D$, and Ring A are as defined in U.S. Pat. No. 9,199,994, the disclosure of which is incorporated herein by reference in its entirety. For example, Intermediate 1 (e.g., 2-benzyl 3-ethyl (S)-2,8-diazaspiro[4.5]decane-2,3-dicarboxylate) is added to a solution of compound A in a solvent (e.g., dioxane) in the presense of a base (e.g., NaHCO₃), and heated to reflux to provide a compound of formula C. In step 2, the $Pg^2$ group (e.g., a carbobenzyloxy (CBZ)) group of formula C is removed (e.g. via reaction with trimethylsilyl iodide (TMSI), a strong acid, or transition metal-catalyzed hydrogenation) to form the desired TPH1-inhibiting compound.

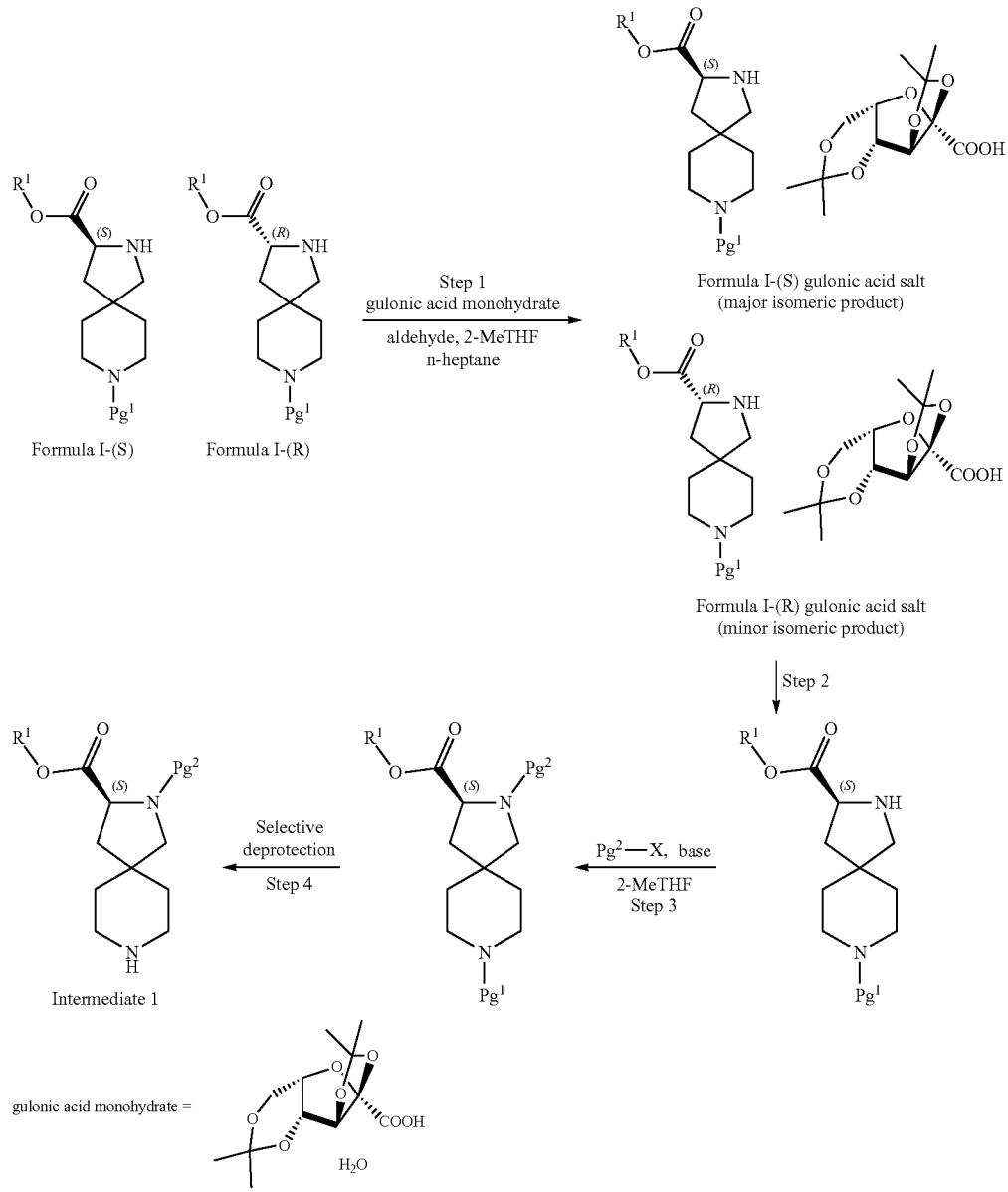

Scheme 3.

Scheme 4.

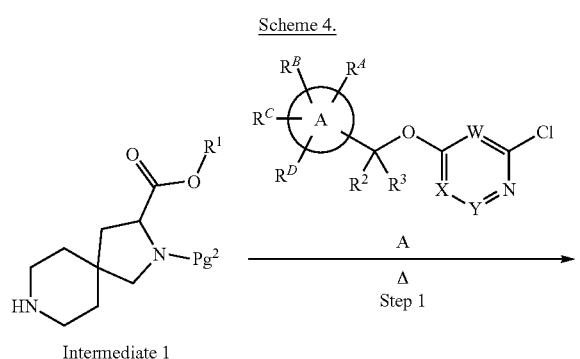

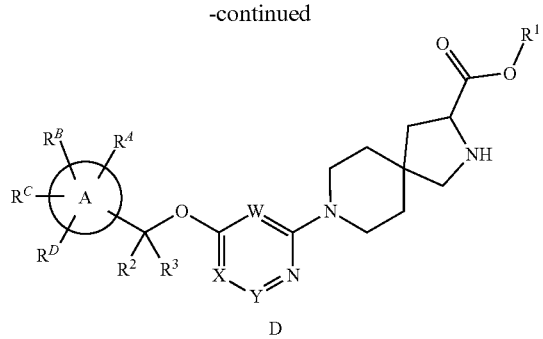

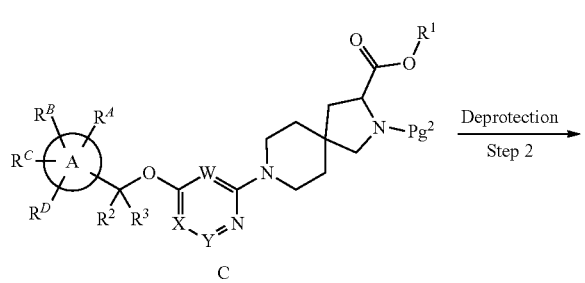

Intermediate 1 of Scheme 3 may also be used in the preparation of TPH1-inhibiting compounds, for example, as shown below in Scheme 5. For example, Intermediate 1 (e.g., 2-benzyl 3-ethyl (S)-2,8-diazaspiro[4.5]decane-2,3-dicarboxylate) is added to a solution of compound A in a solvent (e.g., dioxane) in the presence of a base (e.g., NaHCO$_3$), and heated to reflux to provide a compound of formula B. Subsequent reaction with phenyl boronic acid under standard aryl-aryl coupling conditions (e.g., reaction in the presence of a palladium catalyst such as PdCl$_2$(dppf)-CH$_2$Cl$_2$ in the presence of a base such as KHCO$_3$) affords compound C. The amino protecting group Pg$^2$ group (e.g., a carbobenzyloxy (CBZ)) group of formula C is then removed (e.g., reaction with TMSI) to form the desired TPH1-inhibiting compound of formula D.

Scheme 5.

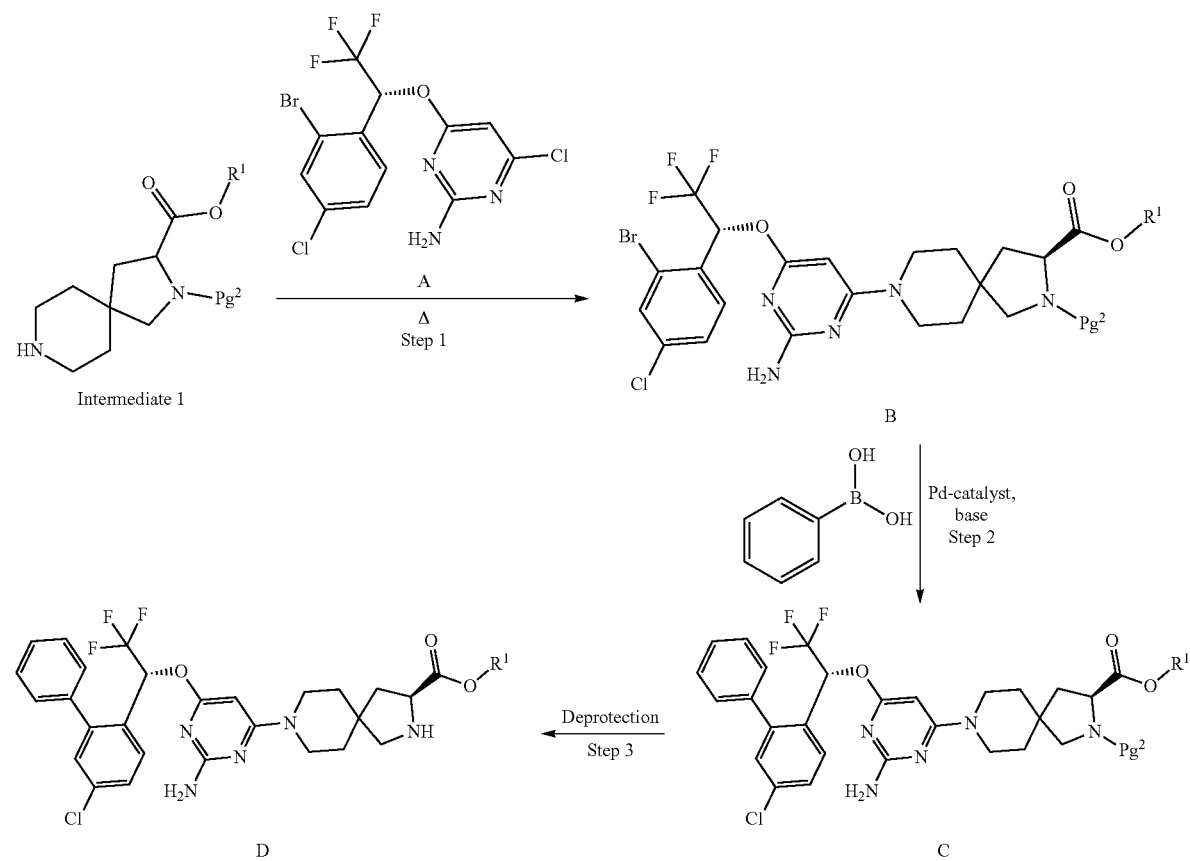

As used herein, the term "amino" refers to a group of formula —NH$_2$.

As used herein, the term "halo" refers to a halogen atom selected from F, Cl, I, and Br. In some embodiments, the halo group is Cl.

As used herein, the term "deprotection" refers to conditions suitable to cleave an amine protecting group. In some embodiments, deprotection may include cleavage of a protecting group in the presence of a strong acid, in the presence of a strong base, in the presence of a reducing agent, or in the presence of an oxidizing agent. For example, deprotection of an amine protecting group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, the deprotecting comprises reacting the protected compound under acidic conditions (e.g., hydrochloric acid or trifluoroacetic acid).

It will be appreciated by one skilled in the art that the processes described are not the exclusive means by which compounds and salts provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis, Vols.* 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991), the disclosures of each of which are incorporated by reference herein in their entireties.

EXAMPLES

The disclosure will be described in greater detail by way of specific examples. The following examples are offered for illustrative purposes, and are not intended to limit the disclosure in any manner. Those of skill in the art will readily recognize a variety of non-critical parameters which can be changed or modified to yield essentially the same results.

HPLC analysis was performed on an Agilent 1100 machine the following conditions: Column: Altima C18, 150 mm length, 3.1 mm diameter 3 μm particle size. Mobile Phase A: 0.1% formic acid in milli-q water. Mobile Phase B: 0.1% formic acid in acetonitrile.

Enantiomeric purity was determined using one of the following conditions:

Enantiomeric Purity Method A: YMC Chiral Amylose-SA column (250 mm length, 4.6 mm diameter, 5 μm particle size) on an Agilent 1100 HPLC machine with n-heptane:isopropanol:ethanol:diethyl amine (80:10:10:0.1, v:v:v:v %) as the eluent.

Enantiomeric Purity Method B: YMC Chiral NEA [NR30S05-2546WT] (250 mm length, 4.6 mm diameter, 5 μm particle size) on an Agilent 11 1100 HPLC machine with 150 mmol/L sodium perchlorate (pH 2.5) in milli-q water and ethanol as the eluent.

Example 1. 8-(tert-butyl) 3-ethyl 2,8-diazaspiro[4.5]decane-3,8-dicarboxylate (Isomeric Mixture)

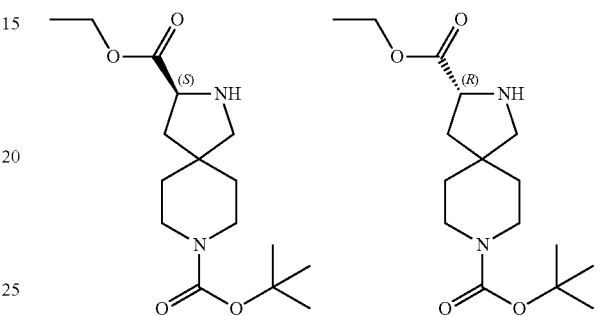

Step 1. ethyl (Z)-3-bromo-2-(hydroxyimino)propanoate

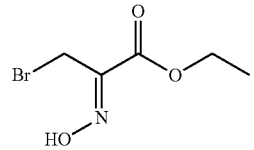

A reactor was charged with hydroxylamine.HCl (13.4 kg, 192.8 mol, 1.25 eq), potable water (2.5 vol) and toluene (5 vol). The mixture was stirred and cooled to about 15° C. ethyl bromopyruvate (29.9 kg, 153.3 mol, 1.0 eq) and toluene (1.5 vol) were added and the mixture was stirred for 16-20 hours between 15-25° C. The phases were then separated after settling for at least 15 minutes. The aqueous layer was removed and the organic layer was maintained in the reactor. The reactor with subsequently charged with potable water (0.5 vol) and the resulting mixture was stirred for at least 15 minutes. The aqueous layer was removed, the organic layer was maintained in the reactor, and the aqueous extraction was performed two additional times. The organic layer was concentrated using vacuum distillation at 35-40° C. (~3.5 vol. removed; 3.6 relative volumes remaining). The reactor was subsequently charged with n-heptane (3 vol) and the resulting solution was concentrated using vacuum distillation at 35-40° C. until about 3.6 relative volumes remained. Additional n-heptane was added (3 vol) and the resulting solution was concentrated using vacuum distillation at 35-40° C. until about 3.6 relative volumes remained. The resulting mixture was then cooled about 10° C. and stirred for about 20-25 minutes. The mixture was filtered and the resulting mother liquor was removed. The reactor was charged with n-heptane (0.73 vol) and stirred for at least 5 minutes. The resulting filter cake was rinsed with n-heptane and dried for at least 5 minutes at ambient temperature. The rinsing and drying steps were repeated, at which time the filter cake was dried for between 0.5-2.5 days under vacuum and nitrogen flow at ambient temperature. HPLC purity: Batch 1: 93.21 area-%. Batch 2: 93.76 area-%. $^1$H-NMR purity (two batches): Batch 1: 51.9 wt-%; Batch 2: 93.7 wt-%.

Step 2. tert-butyl 4-(pyrrolidin-1-ylmethylene)piperidine-1-carboxylate

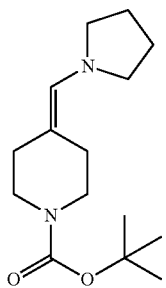 [SMILES: CC(C)(C)OC(=O)N1CCC(=CN2CCCC2)CC1]

The reaction was charged with N-Boc-piperidine-4-carbaldehyde (18.2 kg, 85.3 mol, 1.0 eq) and toluene (16 vol), and the mixture was stirred until dissolution of the N-Boc-piperidine-4-carbaldehyde. Pyrrolidine (10.2 kg, 143.3 mol, 1.6 eq) and additional toluene (0.5 vol) were added, and the resulting mixture was heated to reflux (~111° C.) to remove water via azeotropic distillation. The resulting solution was then concentrated using vacuum distillation between 35-40° C. until 12.2 relative volumes remained. Additional toluene (6 vol) was added, and the resulting solution was concentrated between 35-40° C. until 12.2 relative volumes remained. The resulting mixture was cooled to approximately 20° C. and used in the next step without further purification. Batch 1: 84.1 area-% tert-butyl 4-(pyrrolidin-1-ylmethylene)piperidine-1-carboxylate; 8.8 area-% N-Boc-piperidine-4-carbaldehyde; 7.0 area-% pyrrolidine. KF: <0.1 wt-%. Batch 2: 86.6 area-% tert-butyl 4-(pyrrolidin-1-ylmethylene)piperidine-1-carboxylate; 6.3 area-% N-Boc-piperidine-4-carbaldehyde; 6.2 area-% pyrrolidine. KF: <0.1 wt-%.

Step 3. 9-(tert-butyl) 4-ethyl 1-hydroxy-2-oxa-3,9-diazaspiro[5.5]undec-3-ene-4,9-dicarboxylate

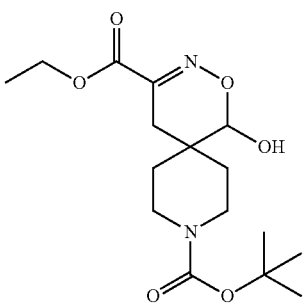 [SMILES: CCOC(=O)C1=NOC(O)C2(CCN(C(=O)OC(C)(C)C)CC2)C1]

A first reactor was charged with ethyl (Z)-3-bromo-2-(hydroxyimino)propanoate (from Example 1, Step 1; Batch 1: 18.81 kg, 89.6 mol, 1.06 eq; Batch 2: 18.9 kg, 90.0 mol, 1.06 eq) and 2-methyltetrahydrofuran (1.7-1.92 vol) and the resulting mixture was stirred and cooled to -5° C. In a second reactor, a solution of tert-butyl 4-(pyrrolidin-1-ylmethylene)piperidine-1-carboxylate in toluene (from Example 1, Step 2; Batch 1: 22.7 kg, 85.3 mol, 1.00 eq. Batch 2: 22.7 kg, 85.3 mol, 1.00 eq.) was cooled to -5° C. and N,N'-diisopropylethylamine (Batch 1: 17.4 kg, 134.2 mol, 1.6 eq. Batch 2: 17.5 kg, 135.4 mol, 1.6 eq.) and toluene (0.5 vol) were added. The solution of (Z)-3-bromo-2-(hydroxyimino)propanoate and 2-methyltetrahydrofuran was then added to the second reactor over about 1-2 hours while maintaining a temperature below 10° C. The first reactor was then rinsed with additional 2-methyltetrahydrofuran (0.22 vol) which was added to the second reactor. Upon complete addition of the (Z)-3-bromo-2-(hydroxyimino)propanoate solution to the second reactor, the resulting mixture was heated to about 15° C. and stirred for about 45 minutes. Aqueous hydrochloric acid solution (30% HCl prepared from 2.2 eq. HCl and 3.5 vol of potable water) was added to the reaction mixture (Batch 1: 24.2 kg, 199.1 mol, 2.3 eq; Batch 2: 23.9 kg, 196.7 mol, 2.3 eq.) and the resulting mixture was heated to 30° C. and stirred for about 45 minutes. The organic and aqueous phases were separated after allowing settling for at least 15 minutes and the aqueous layer was removed. The organic phase was washed with potable water (1.0 vol) and the mixture was stirred for at least 5 minutes. The phases were separated after allowing settling for at least 10 minutes and the aqueous phase was removed and further extracted with additional 2-methyltetrahydrofuran (5 vol). The organic layers were combined, washed with an additional portion of potable water (1 vol), and the aqueous phase was removed. The resulting combined organic phases were concentrated using vacuum distillation between 35-40° C. until about 5.4 relative volumes remained, at which time n-heptane (3 vol) was added and the resulting mixture was concentrated at 35-40° C. until about 5.4 relative volumes remained. Addition of n-heptane and vacuum distillation was repeated, at which time additional n-heptane (3 vol) was added and the resulting mixture was cooled to about 20° C. The mixture was filtered, and the resulting filter cake was washed with n-heptane (2.57 vol) and toluene (0.14 vol) (2×). The filter cake was dried, washed with an additional portion of n-heptane (2.57 vol), and stirred. The n-heptane was then removed and the resulting filter cake was dried under nitrogen for between 18-72 hours at ambient temperature and used in the next step without further purification. Batch 1: HPLC purity: 98.37 area-%. $^1$H-NMR: 91.8 wt %. Batch 2: HPLC purity: 99.52 area-%. $^1$H-NMR: 90.7 wt %.

Step 4. 8-(tert-butyl) 3-ethyl 2,8-diazaspiro[4.5]decane-3,8-dicarboxylate (Isomeric Mixture)

A reactor was charged with 9-(tert-butyl) 4-ethyl 1-hydroxy-2-oxa-3,9-diazaspiro[5.5]undec-3-ene-4,9-dicarboxylate (from Example 1, Step 3, 38.2 kg, 111.8 mol, 1.0 eq), ethanol (abs., 4 vol) and tetrahydrofuran (4 vol) and the mixture was stirred. Sponge catalyst A5000 (28.9 kg) was then added and the reactor was purged several times with vacuum and nitrogen and then purged with vacuum and hydrogen. The resulting mixture was then heated to about 30° C. and the reactor was pressurized with hydrogen to 4±0.5 bar and the mixture was stirred for about 16-22 hours at 30±5° C. under hydrogen. The reactor was then depressurized and charged with nitrogen. The reactor was then purged with vacuum and hydrogen, pressurized with hydrogen to 4±0.5 bar, and stirring was continued for about 46 hours at 30±5° C. under hydrogen. The reactor was depressurized and the reaction mixture was filtered over a dicalite filter and rinsed with 2-methyltetrahydrofuran. The filtrate was collected, washed with additional 2-methyltetrahydrofuran, and concentrated under reduced pressure between 35-40° C. until about 3.75 relative volumes remained. The distillation process was repeated two additional times at which time the resulting mixture was cooled to about 20° C. and the resulting product was used without further purification. HPLC purity: 78.8 area-%.

Example 2A. 8-(tert-butyl) 3-ethyl 2,8-diazaspiro [4.5]decane-3,8-dicarboxylate, 2,3:4,6-di-O-isopropylidene-2-keto-L-gulonic acid salt (Isomeric mixture enriched in the (S)-isomer)

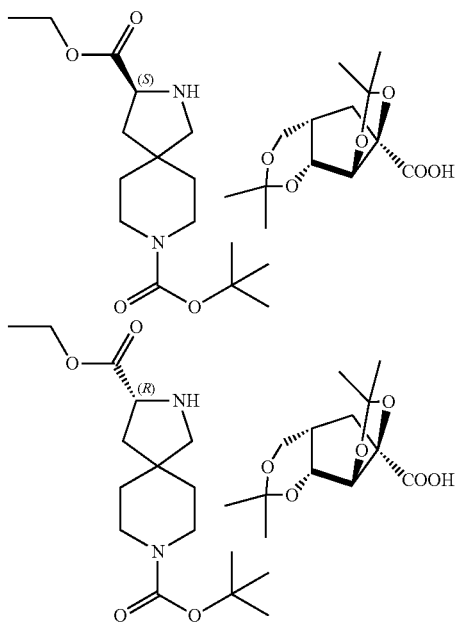

A reactor was charged with 2,3:4,6-di-O-isopropylidene-2-keto-L-gulonic acid monohydrate (32.65 kg, 111.5 mol, 1.0 eq), 2-methyltetrahydrofuran (2 vol), and benzaldehyde (0.04 vol). Next, a solution of the 8-(tert-butyl) 3-ethyl 2,8-diazaspiro[4.5]decane-3,8-dicarboxylate (isomeric mixture of Example 1) was added with additional 2-methyltetrahydrofuran (1 vol). The resulting mixture was stirred and heated at 28° C. until a solution was formed. The solution was then stirred for at least 30 minutes at 40±3° C. The resulting mixture was then cooled to 30±3° C. and stirred for an additional 2 hours. The mixture was then seeded with 8-(tert-butyl) 3-ethyl (S)-2,8-diazaspiro[4.5]decane-3,8-dicarboxylate, 2,3:4,6-di-O-isopropylidene-2-keto-L-gulonic acid salt (2 g), and the resulting mixture was stirred for about 14-15 hours at 30±3° C. The reaction mixture was then cooled to about 20±3° C. over 4 hours and then stirred for an additional 15 hours. The mixture was filtered and the filtrate was separated for further reaction. The resulting filter cake was washed with 2-methyltetrahydrofuran (1 vol, 3×) and dried for 5 minutes between each addition of 2-methyltetrahydrofuran to afford a mixture of 8-(tert-butyl) 3-ethyl 2,8-diazaspiro[4.5]decane-3,8-dicarboxylate 2,3:4,6-di-O-isopropylidene-2-keto-L-gulonic acid isomers enriched in the 8-(tert-butyl) 3-ethyl (S)-2,8-diazaspiro[4.5]decane-3,8-dicarboxylate, 2,3:4,6-di-O-isopropylidene-2-keto-L-gulonic acid salt. HPLC purity: 95.67 area-%. Enantiomeric purity of the (S-) isomer: 78.55 area-%. The separated filtrate was separately concentrated between 35-40° C. until 3.5 relative volumes remained and the mixture was cooled to 27.5° C. The mixture was then seeded with 8-(tert-butyl) 3-ethyl (S)-2,8-diazaspiro[4.5]decane-3,8-dicarboxylate, 2,3:4,6-di-O-isopropylidene-2-keto-L-gulonic acid salt and stirred for at least 16 hours at 20±3° C. The resulting mixture was filtered, the filtrate was removed, and the resulting filter cake was washed with 2-methyltetrahydrofuran (0.57 vol) and dried (3×) to afford a second crop of a mixture of 8-(tert-butyl) 3-ethyl 2,8-diazaspiro[4.5]decane-3,8-dicarboxylate 2,3:4,6-di-O-isopropylidene-2-keto-L-gulonic acid isomers enriched in the 8-(tert-butyl) 3-ethyl (S)-2,8-diazaspiro[4.5]decane-3,8-dicarboxylate, 2,3:4,6-di-O-isopropylidene-2-keto-L-gulonic acid salt. HPLC purity: 98.29 area-%; Enantiomeric purity of the (S-) isomer (Method A): 93.60 area-%. Volumes and molar ratios provided are relative to the isomeric mixture of 8-(tert-butyl) 3-ethyl 2,8-diazaspiro[4.5]decane-3,8-dicarboxylate prepared in Example 1.

The obtained mixture of 8-(tert-butyl) 3-ethyl 2,8-diazaspiro[4.5]decane-3,8-dicarboxylate 2,3:4,6-di-O-isopropylidene-2-keto-L-gulonic acid isomers (23.2 kg, 39.5 mol, 1.0 eq) was then added to a reactor with 2-methyltetrahydrofuran (16 vol) and the mixture was heated to reflux (about 80° C.) until the solids dissolved. The mixture was then cooled to 40±3° C. over about 2 hours and crystallization was observed. The mixture was then concentrated between 35-40° C. until about 9 relative volumes remained. The mixture was then cooled to 20±3° C. and stirring was continued for about 2-3 hours. The resulting mixture was filtered and rinsed with 2-methyltetrahydrofuran (1.4 vol, 2× with drying under nitrogen for 5 minutes between each washing). The filter cake was then dried under nitrogen for about 14-16 hours to afford the desired mixture of 8-(tert-butyl) 3-ethyl 2,8-diazaspiro[4.5]decane-3,8-dicarboxylate 2,3:4,6-di-O-isopropylidene-2-keto-L-gulonic acid isomers enriched in the 8-(tert-butyl) 3-ethyl (S)-2,8-diazaspiro[4.5]decane-3,8-dicarboxylate, 2,3:4,6-di-O-isopropylidene-2-keto-L-gulonic acid salt. Batch 1: HPLC purity: 99.49 area-%; Enantiomeric purity of the (S-) isomer (Method A): 93.98 area-%. Batch 2: HPLC purity: >99.9 area-%; Enantiomeric purity of the (S-) isomer (Method A): 95.22 area-%. A second recrystallization of the 8-(tert-butyl) 3-ethyl 2,8-diazaspiro[4.5]decane-3,8-dicarboxylate 2,3:4,6-di-O-isopropylidene-2-keto-L-gulonic acid isomers was performed which further enriched the isomeric mixture in the (S-) isomer. Batch 1: HPLC purity: 99.49 area-%; Enantiomeric purity of the (S-) isomer (Method A): 99.02 area-%. Batch 2: HPLC purity: 99.95 area-%; Enantiomeric purity of the (S-) isomer (Method A): 99.48 area-%.

Example 2B

Alternate Preparation of 8-(tert-butyl) 3-ethyl (S)-2,8-diazaspiro[4.5]decane-3,8-dicarboxylate, 2,3:4,6-di-O-isopropylidene-2-keto-L-gulonic acid salt 8-(tert-Butyl) 3-ethyl 2,8-diazaspiro[4.5]decane-3,8-dicarboxylate (1 g, 3.20 mmol) was dissolved in THF (5 vol, 5 ml) at r.t. The solution was treated with 1 molar equivalent of 2,3:4,6-di-O-isopropylidene-2-keto-L-gulonic acid monohydrate and then the temperature was slowly raised to 40° C. After 20 min, a precipitate started to form at 40° C. at which time, TBME (5 vol, 5 ml) was added to the mixture after which time, the reaction was slowly cooled to 5° C. at a rate of 1° C./min. After this time, the solid formed was filtered and then washed with cold TBME. The solid was dried in vacuo to provide 8-(tert-butyl) 3-ethyl (S)-2,8-diazaspiro[4.5]decane-3,8-dicarboxylate, 2,3:4,6-di-O-isopropylidene-2-keto-L-gulonic acid salt (45%, >99% ee) as a crystalline solid suitable for seeding.

Example 3. 8-(tert-butyl) 3-ethyl (S)-2,8-diazaspiro[4.5]decane-3,8-dicarboxylate

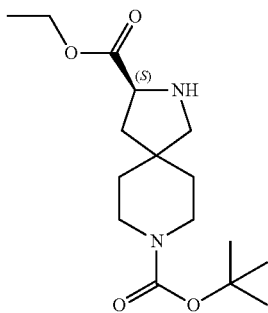

A reactor was charged with the enriched mixture of 8-(tert-butyl) 3-ethyl 2,8-diazaspiro[4.5]decane-3,8-dicarboxylate 2,3:4,6-di-O-isopropylidene-2-keto-L-gulonic acid isomers (Example 2, 23.80 kg, 40.5 mol, 1.0 eq), 2-methyltetrahydrofuran (2 vol), and n-heptane (8 vol), and the mixture was stirred at 15±3° C. Sodium carbonate (10% solution in water; 125.8 kg) was added over 15 minutes while maintaining the temperature of the reaction mixture between 15-20° C. and the resulting mixture was stirred for at least 35 minutes. The phases were separated and the aqueous phase was removed. To the remaining organic phase was added additional sodium carbonate (10% solution in water; 27.4 kg) while maintaining the temperature of the reaction mixture between 15-20° C. and the resulting mixture was stirred for at least 35 minutes. The phases were separated, the aqueous phase was removed, and the organic phase was concentrated to dryness to afford the title compound. HPLC purity: 97.65 area-%. Enantiomeric purity of the (S-) isomer (Method A): 98.89 area-%. Volumes and molar ratios provided are relative to the 8-(tert-butyl) 3-ethyl 2,8-diazaspiro[4.5]decane-3,8-dicarboxylate 2,3:4,6-di-O-isopropylidene-2-keto-L-gulonic acid isomers prepared in Example 2A.

Example 4. 2-benzyl 8-(tert-butyl) 3-ethyl (S)-2,8-diazaspiro[4.5]decane-2,3,8-tricarboxylate

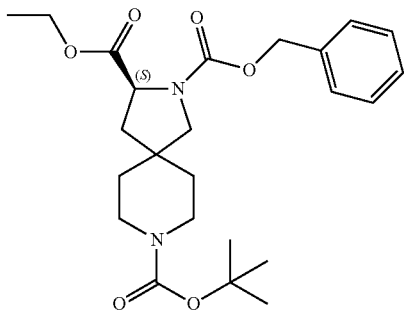

A reactor was charged with 8-(tert-butyl) 3-ethyl (S)-2,8-diazaspiro[4.5]decane-3,8-dicarboxylate (Example 3, 12.6 kg, 32.2 mol, 1.0 eq.), sodium carbonate (10% in water, 86.4 kg), and 2-methyltetrahydrofuran (0.55 rel. vol), and the mixture was cooled to 0±3° C. A solution of benzyl chloroformate (6.7 kg, 38.76 mol, 1.0 eq) in 2-methyltetrahydrofuran (0.25 vol) was then added over 40 minutes while maintaining the temperature of the reaction mixture between −2-2° C. Additional 2-methyltetrahydrofuran (0.25 vol) was used to rinse residual benzyl chloroformate solution into the reaction mixture, and the resulting mixture was stirred for 5-10 minutes at 0±3° C. The mixture was then heated to to 30±3° C. and stirred for an additional 20-30 minutes. The phases were then separated and the aqueous phase was removed. The organic phase was washed with a portion of potable water (1 vol) and the mixture was heated to 30±3° C. and stirred for at least 5 minutes. The aqueous phase was then removed and the remaining organic phase was concentrated using vacuum distillation between 35-40° until about 3 relative volumes remained. Absolute ethanol (3 vol) was then added and the resulting mixture was concentrated using vacuum distillation between 35-40° until about 3 relative volumes remained. The addition of ethanol and distillation was performed a second time to afford the title product. HPLC purity: 65.58 area-%. The deprotected compound, 2-benzyl 3-ethyl (S)-2,8-diazaspiro[4.5]decane-2,3-dicarboxylate was also observed. The combined HPLC purity of the title product and the BOC-deprotected product was 80.45 area-%.

Example 5. 2-benzyl 3-ethyl (S)-2,8-diazaspiro[4.5]decane-2,3-dicarboxylate hydrochloride

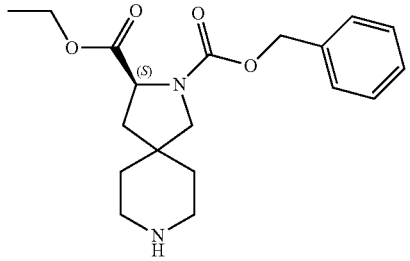

A reactor was charged with absolute ethanol (67 kg, 3.75 vol) and cooled to about 12.5° C. Acetyl chloride (10.0 kg, 6.00 eq) was added over 55 minutes, while maintaining the temperature of the mixture below 15° C. Ethyl acetate (10.2 kg, 0.5 vol) was added, and the mixture was stirred for 15-25 minutes while increasing the temperature to 17° C. Next, a solution of 2-benzyl 8-(tert-butyl) 3-ethyl (S)-2,8-diazaspiro[4.5]decane-2,3,8-tricarboxylate in ethanol (Example 4, 17.3 kg of 2-benzyl 8-(tert-butyl) 3-ethyl (S)-2,8-diazaspiro[4.5]decane-2,3,8-tricarboxylate; total solution of 2-benzyl 8-(tert-butyl) 3-ethyl (S)-2,8-diazaspiro[4.5]decane-2,3,8-tricarboxylate and ethanol: 87 kg) was added over 25 minutes while maintaining the temperature of the reaction mixture at about 16° C. Additional absolute ethanol (0.5 vol) was added and the reaction mixture was heated to 30±3° C. and stirred for about 16 hours. The mixture was then concentrated using vacuum distillation between 35-40° C. until about 4 relative volumes remained. 2-methyltetrahydrofuran (3 vol) was added, and the resulting mixture was concentrated using vacuum distillation between 35-40° C. until about 4 relative volumes remained. The addition of 2-methyltetrahydrofuran and distillation was performed three times using 3 vol of 2-methyltetrahydrofuran and a final time using 2 vol of 2-methyltetrahydrofuran. The reaction mixture was then heated to about 30-35° C. and stirred for about 40 minutes. Additional 2-methyltetrahydrofuran (1.5 vol) was then added while maintaining the temperature at about 29° C. The mixture was cooled to 25±3° C. over a period of 1 h, then stirred for about 18 hours. The mixture was filtered and the filter cake was washed with 2-methyltetrahydrofuran (1.0 vol) and stirred for at least 5 minutes. The washing was repeated with the filter cake drying for at least 5 minutes between washes. The filter cake was then dried under nitrogen flow for about 19 hours at ambient temperature to afford the title product. HPLC purity: 99.09%. Chiral purity (Method B): 99.85%. Enantiomeric excess of (S-) isomer (Method B): ≥98%.

A second crop of the title compound was prepared by combining the filtrates and wash solvents and concentrated to about 35 L followed by addition of 35 L of methyl tert-butyl ether (MTBE) over 45 minutes. The mixture was then stirred for 1 hour at 25° C. and filtered. The resulting filter cake was washed with additional MTBE and dried for 17 hours to afford a second crop of the title product. HPLC purity: 98.56%. Chiral purity (Method B): 99.27%. Enantiomeric excess of the (S-) isomer (Method B): ≥98%.

Example 6. (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate

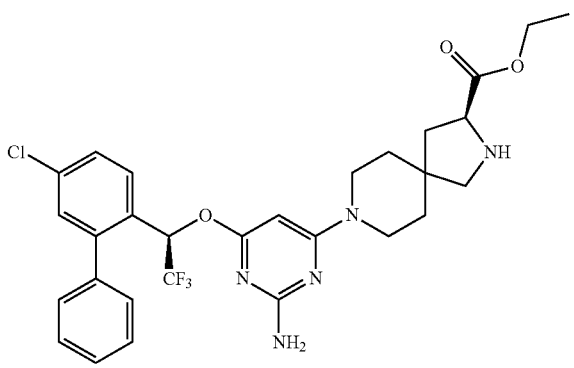 [SMILES: CCOC(=O)[C@@H]1CC2(CCN(c3cc(O[C@H](c4ccc(Cl)cc4-c4ccccc4)C(F)(F)F)nc(N)n3)CC2)CN1]

The title compound was prepared from 2-benzyl 3-ethyl (S)-2,8-diazaspiro[4.5]decane-2,3-dicarboxylate hydrochloride (Example 5) according to the procedures shown in Scheme 5 and in U.S. Pat. No. 9,199,994, the disclosure of which is incorporated herein by reference in its entirety. The title compound has been found to be an inhibitor of TPH1 according to one or more assays described in U.S. Pat. No. 9,199,994.

Various modifications of the disclosure, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A process of increasing the amount of an acid salt of an isomeric compound of Formula I-(S):

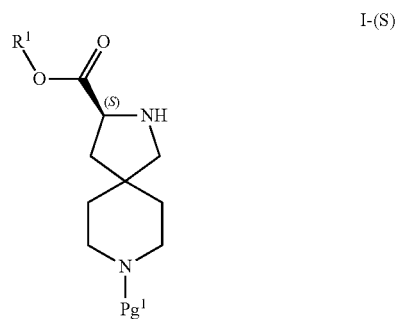

wherein $R^1$ is $C_{1-6}$ alkyl and $Pg^1$ is an amino protecting group, relative to an amount of an acid salt of an isomeric compound of Formula I-(R):

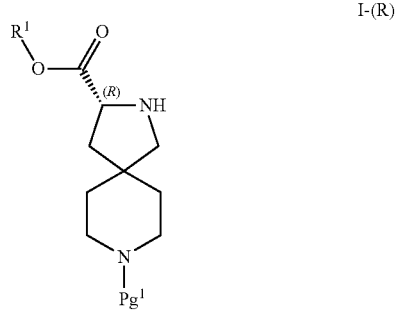

in a starting mixture comprising both isomeric compounds of Formula I-(S) and Formula I-(R), the process comprising:
reacting the starting mixture with 2,3:4,6-di-O-isopropylidene-2-keto-L-gulonic acid, or a hydrate thereof, in the presence of an aldehyde in an organic solvent to form an acid salt mixture comprising 2,3:4,6-di-O-isopropylidene-2-keto-L-gulonic acid salts of the isomeric compounds,
and
filtering the acid salt mixture to obtain a sold acid salt mixture,
wherein the solid acid salt mixture has an increased amount of the gulonic acid salt of the isomeric compound of Formula I-(S) relative to the amount of gulonic acid salt of the isomeric compound of Formula I-(R) when compared with the relative amounts of the isomeric compounds of Formulas I-(S) and I-(R) present in the starting mixture, wherein the enantiomeric excess of the gulonic acid salt of the isomeric compound of Formula I-(S) in the salt mixture is 95% or greater, wherein the organic solvent is selected from the group consisting of tetrahydrofuran, 2-methyltetrahydrofuran, and a mixture of tetrahydrofuran or 2-methyltetrahydrofuran with an additional solvent.

2. The process of claim 1, wherein the 2,3:4,6-di-O-isopropylidene-2-keto-L-gulonic acid, or a hydrate thereof, is 2,3:4,6-di-O-isopropylidene-2-keto-L-gulonic acid monohydrate.

3. The process of claim 1, wherein the reacting is carried out with about 1 molar equivalent of the 2,3:4,6-di-O-isopropylidene-2-keto-L-gulonic acid, or a hydrate thereof, with respect to the combined amount of both isomeric compounds of Formula I-(S) and Formula I-(R) in the starting mixture.

4. The process of claim 1, wherein the aldehyde is benzaldehyde.

5. The process of claim 1, wherein the reacting is carried out with less than 1 molar equivalent of the aldehyde with respect to the combined amount of both isomeric compounds of Formula I-(S) and Formula I-(R) in the starting mixture.

6. The process of claim 1, wherein the reacting is carried out with about 0.01 to about 0.1 molar equivalents of the aldehyde with respect to the combined amount of both isomeric compounds of Formula I-(S) and Formula I-(R) in the starting mixture.

7. The process of claim 1, wherein the reacting is carried out at a temperature of about 30° C. to about 40° C.

8. The process of claim 1, wherein the reacting is carried out in the presence of tetrahydrofuran.

9. The process of claim 1, wherein the reacting is carried out in the presence of 2 methyltetrahydrofuran.

10. The process of claim 1, wherein the enantiomeric excess of the gulonic acid salt of the isomeric compound of Formula I-(S) in the salt mixture is 97% or greater.

11. The process of claim 1, further comprising recrystallizing the salt mixture to form a purified salt mixture having an increased amount of the gulonic acid salt of the isomeric compound of Formula I-(S) relative to the gulonic acid salt of the isomeric compound of Formula I-(R) when compared with the relative amounts of the gulonic acid salts of the isomeric compounds prior to the purification.

12. The process of claim 11, wherein the enantiomeric excess of the gulonic acid salt of the isomeric compound of Formula I-(S) is 97% or greater.

13. The process of claim 11, further comprising reacting the purified salt mixture with a base to form a freebased mixture comprising isomeric compounds having Formula I-(S) and Formula I-(R):

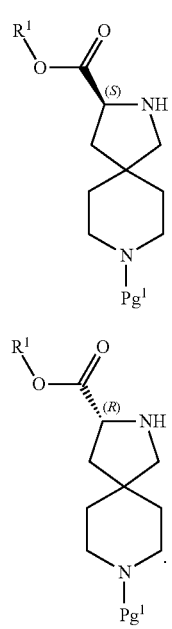

14. The process of claim 13, wherein the base is in the form of an aqueous solution.

15. The process of claim 13, wherein the base is an aqueous solution of sodium carbonate.

16. The process of claim 13, wherein the reacting of the purified salt mixture is carried out with a molar excess amount of base with respect to the combined amount of both gulonic acid salts of the isomeric compounds of Formula I-(S) and Formula I-(R) in the salt mixture.

17. The process of claim 13, wherein the reacting of the purified salt mixture is carried out in the presence of a second organic solvent.

18. The process of claim 13, wherein the reacting of the purified salt mixture is carried out in the presence of a second organic solvent comprising an ether solvent and a hydrocarbon solvent.

19. The process of claim 13, wherein the reacting of the purified salt mixture is carried out in the presence of a second organic solvent comprising 2-methyltetrahydrofuran and n-heptane.

20. The process of claim 13, wherein the enantiomeric excess of the isomeric compound of Formula I-(S) in the freebased mixture is 97% or greater.

21. The process of claim 1, wherein $R^1$ is ethyl.

22. The process of claim 1, wherein $Pg^1$ is tert-butoxycarbonyl.

23. A process of increasing the amount of an isomeric compound of Formula Ia-(S):

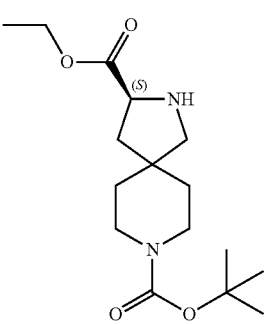

relative to an amount of an isomeric compound of Formula Ia-(R):

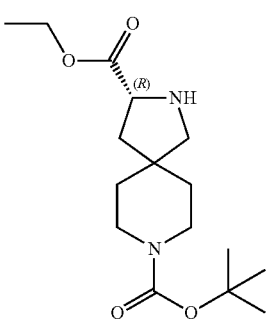

in a starting mixture comprising both isomeric compounds of Formula Ia-(S) and Formula Ia-(R), the process comprising:
(a) reacting the starting mixture in an organic solvent with 2,3:4,6-di-O-isopropylidene-2-keto-L-gulonic acid monohydrate in the presence of benzaldehyde to form a salt mixture comprising 2,3:4,6-di-O-isopropylidene-2-keto-L-gulonic acid salts of the isomeric compounds, and filtering the acid salt mixture to obtain a sold acid salt mixture, wherein the solid salt mixture has an increased amount of the gulonic acid salt of the isomeric compound of Formula Ia-(S) relative to the amount of gulonic acid salt of the isomeric compound of Formula Ia-(R) when compared with the relative amounts of the isomeric compounds of Formulas Ia-(S) and Ia-(R) present in the starting mixture, wherein the organic solvent is selected from the group consisting of tetrahydrofuran, 2-methyltetrahydrofuran, and a mixture of tetrahydrofuran or 2-methyltetrahydrofuran with an additional solvent;

(b) recrystallizing the salt mixture to form a purified salt mixture having an increased amount of the gulonic acid salt of the isomeric compound of Formula Ia-(S) relative to the gulonic acid salt of the isomeric compound of Formula Ia-(R) when compared with the relative amounts of the gulonic acid salts of the isomeric compounds prior to the purification; and reacting the purified salt mixture in the presence of sodium carbonate to form a freebased mixture comprising isomeric compounds having Formula Ia-(S) and Formula Ia-(R), wherein the enantiomeric excess of the isomeric compound of Formula Ia-(S) in the freebased mixture is 95% or greater.

24. The process of claim 1, wherein the enantiomeric excess of the gulonic acid salt of the isomeric compound of Formula I-(S) in the salt mixture is 95% to about 99.9%.

25. The process of claim 23, wherein the enantiomeric excess of the isomeric compound of Formula I-(S) in the freebased mixture is 95% to about 99.9%.

* * * * *